(12) United States Patent
Greenburg et al.

(10) Patent No.: US 9,113,813 B2
(45) Date of Patent: *Aug. 25, 2015

(54) LOCATABLE CATHETER

(71) Applicant: COVIDIEN LP, Mansfield, MA (US)

(72) Inventors: Benny Greenburg, Hod HaSharon (IL); Dorian Averbuch, Ramat HaSharon (IL); Oded Zur, Kochav-Ya'ir Zur Yigal (IL)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/109,244

(22) Filed: Dec. 17, 2013

(65) Prior Publication Data

US 2014/0107465 A1 Apr. 17, 2014

Related U.S. Application Data

(63) Continuation of application No. 12/755,332, filed on Apr. 6, 2010, now Pat. No. 8,611,984.

(60) Provisional application No. 61/167,839, filed on Apr. 8, 2009.

(51) Int. Cl.
| | |
|---|---|
| *A61M 25/095* | (2006.01) |
| *A61B 5/06* | (2006.01) |
| *A61B 5/05* | (2006.01) |
| *A61B 5/00* | (2006.01) |
| *A61B 19/00* | (2006.01) |
| *A61B 1/018* | (2006.01) |

(Continued)

(52) U.S. Cl.
CPC .................. *A61B 5/062* (2013.01); *A61B 1/018* (2013.01); *A61B 1/2676* (2013.01); *A61B 5/05* (2013.01); *A61B 5/6852* (2013.01); *A61B 19/5244* (2013.01); *A61M 25/0127* (2013.01); *A61B 2019/5251* (2013.01); *A61B 2019/5483* (2013.01)

(58) Field of Classification Search
CPC ............ A61B 5/06; A61B 5/062; A61B 5/05; A61B 5/6852; A61B 19/5244; A61B 2019/5251; A61B 2019/5483; A61B 1/018; A61B 1/2676; G01R 33/285; G01R 33/02; A61M 25/0127

See application file for complete search history.

(56) References Cited

U.S. PATENT DOCUMENTS

| | | | |
|---|---|---|---|
| 1,576,781 | A | 3/1926 | Phillips |
| 1,735,726 | A | 11/1929 | Bornhardt |

(Continued)

FOREIGN PATENT DOCUMENTS

| | | |
|---|---|---|
| CA | 964149 | 3/1975 |
| DE | 3042343 A1 | 6/1982 |

(Continued)

OTHER PUBLICATIONS

EP Partial Search Report in corresponding EP 10 159 373.9, dated Jul. 14, 2010.

(Continued)

*Primary Examiner* — Elmer Chao

(57) ABSTRACT

A catheter having a sensor at a distal end thereof, useable to detect and create signals from an electromagnetic field. The sensor is constructed and arranged to leave a lumen of the catheter open such that it may be used to pass instruments therethrough once a target location has been reached.

13 Claims, 2 Drawing Sheets

(51) Int. Cl.
*A61B 1/267* (2006.01)
*A61M 25/01* (2006.01)

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,447,224 A | 5/1984 | DeCant, Jr. et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,769,005 A | 9/1988 | Ginsburg et al. |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |

(56) References Cited

U.S. PATENT DOCUMENTS

| | | |
|---|---|---|
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,403,321 A | 4/1995 | DiMarco |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,494,034 A | 2/1996 | Schlondorff et al. |

(56) References Cited

U.S. PATENT DOCUMENTS

| | | |
|---|---|---|
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |

(56) References Cited

U.S. PATENT DOCUMENTS

| | | |
|---|---|---|
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,964,793 A * | 10/1999 | Rutten et al. .................. 607/119 |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,112,111 A | 8/2000 | Glantz |
| 6,118,845 A | 9/2000 | Simon et al. |
| 6,122,538 A | 9/2000 | Sliwa, Jr. et al. |
| 6,122,541 A | 9/2000 | Cosman et al. |
| 6,129,698 A | 10/2000 | Beck |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,192,280 B1 | 2/2001 | Sommer et al. |
| 6,194,639 B1 | 2/2001 | Botella et al. |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,211,666 B1 | 4/2001 | Acker |
| 6,213,995 B1 | 4/2001 | Steen et al. |
| 6,216,026 B1 * | 4/2001 | Kuhn et al. .................. 600/409 |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,304,769 B1 | 10/2001 | Arenson et al. |
| 6,314,310 B1 | 11/2001 | Ben-Haim et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,351,659 B1 | 2/2002 | Vilsmeier |
| 6,366,799 B1 | 4/2002 | Acker et al. |
| 6,373,240 B1 | 4/2002 | Govari |
| 6,381,485 B1 | 4/2002 | Hunter et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,534,982 B1 | 3/2003 | Jakab |
| 6,551,325 B2 | 4/2003 | Neubauer et al. |
| 6,580,938 B1 | 6/2003 | Acker |
| 6,584,174 B2 | 6/2003 | Schubert et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,618,612 B1 | 9/2003 | Acker et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,711,429 B1 | 3/2004 | Gilboa et al. |
| 6,788,967 B2 | 9/2004 | Ben-Haim et al. |
| 6,834,201 B2 | 12/2004 | Gillies et al. |
| 6,995,729 B2 | 2/2006 | Govari et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,248,914 B2 | 7/2007 | Hastings et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,657,300 B2 | 2/2010 | Hunter et al. |
| 7,659,912 B2 | 2/2010 | Akimoto et al. |

(56) References Cited

U.S. PATENT DOCUMENTS

| | | |
|---|---|---|
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,720,521 B2 | 5/2010 | Chang et al. |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,809,421 B1 | 10/2010 | Govari |
| 8,611,984 B2 | 12/2013 | Greenburg et al. |
| 2001/0007918 A1 | 7/2001 | Vilsmeier et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2002/0062203 A1 | 5/2002 | Gilboa |
| 2002/0095081 A1 | 7/2002 | Vilsmeier |
| 2002/0128565 A1 | 9/2002 | Rudy |
| 2002/0173689 A1 | 11/2002 | Kaplan |
| 2002/0193686 A1 | 12/2002 | Gilboa |
| 2003/0018251 A1 | 1/2003 | Solomon |
| 2003/0074011 A1 | 4/2003 | Gilboa et al. |
| 2003/0086599 A1 | 5/2003 | Armato et al. |
| 2003/0142753 A1 | 7/2003 | Gunday |
| 2003/0160721 A1 | 8/2003 | Gilboa et al. |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2005/0033149 A1 | 2/2005 | Strommer et al. |
| 2005/0085715 A1 | 4/2005 | Dukesherer et al. |
| 2005/0107688 A1 | 5/2005 | Strommer |
| 2005/0119527 A1 | 6/2005 | Banik et al. |
| 2005/0197566 A1 | 9/2005 | Strommer et al. |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0149134 A1 | 7/2006 | Soper et al. |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0265639 A1 | 11/2007 | Danek et al. |
| 2007/0287901 A1 | 12/2007 | Strommer et al. |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2009/0182224 A1 | 7/2009 | Shmarak et al. |

FOREIGN PATENT DOCUMENTS

| | | |
|---|---|---|
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |
| EP | 0581704 A1 | 2/1994 |
| EP | 0651968 A1 | 5/1995 |
| EP | 0655138 A1 | 5/1995 |
| EP | 0894473 A2 | 2/1999 |
| EP | 0908146 A2 | 4/1999 |
| EP | 0930046 A2 | 7/1999 |
| EP | 1078644 A1 | 2/2001 |
| EP | 2096523 A1 | 9/2009 |
| FR | 2417970 A1 | 9/1979 |
| FR | 2618211 A1 | 1/1989 |
| GB | 2094590 A | 9/1982 |
| GB | 2164856 A | 4/1986 |
| JP | 63-240851 A | 10/1988 |
| JP | 03-267054 A | 11/1991 |
| JP | 06194639 A | 7/1994 |
| WO | 88/09151 A1 | 12/1988 |
| WO | 89/05123 A1 | 6/1989 |
| WO | 90/05494 A1 | 5/1990 |
| WO | 91/03982 A1 | 4/1991 |
| WO | 91/04711 A1 | 4/1991 |
| WO | 91/07726 A1 | 5/1991 |
| WO | 92/03090 A1 | 3/1992 |
| WO | 92/06645 A1 | 4/1992 |
| WO | 94/04938 A1 | 3/1994 |
| WO | 94/23647 A1 | 10/1994 |
| WO | 94/24933 A1 | 11/1994 |
| WO | 95/07055 A1 | 3/1995 |
| WO | 9605768 A1 | 2/1996 |
| WO | 96/11624 A2 | 4/1996 |
| WO | 96/32059 A1 | 10/1996 |
| WO | 9700043 A1 | 1/1997 |
| WO | 97/29684 A1 | 8/1997 |
| WO | 9729684 A1 | 8/1997 |
| WO | 97/36192 A1 | 10/1997 |
| WO | 97/49453 A1 | 12/1997 |
| WO | 98/08554 A1 | 3/1998 |
| WO | 98/38908 A1 | 9/1998 |
| WO | 99/15097 A2 | 4/1999 |
| WO | 9918852 A1 | 4/1999 |
| WO | 99/21498 A1 | 5/1999 |
| WO | 99/23956 A1 | 5/1999 |
| WO | 99/26549 A1 | 6/1999 |
| WO | 99/27839 A2 | 6/1999 |
| WO | 99/29253 A1 | 6/1999 |
| WO | 99/33406 A1 | 7/1999 |
| WO | 99/37208 A1 | 7/1999 |
| WO | 99/38449 A1 | 8/1999 |
| WO | 99/52094 A1 | 10/1999 |
| WO | 99/60939 A1 | 12/1999 |
| WO | 00/06701 A1 | 2/2000 |
| WO | 0010456 A1 | 3/2000 |
| WO | 00/35531 A1 | 6/2000 |
| WO | 01/30437 A1 | 5/2001 |
| WO | 01/87136 A2 | 11/2001 |
| WO | 02/064011 A2 | 8/2002 |

(56) References Cited

FOREIGN PATENT DOCUMENTS

| WO | 02/070047 | A1 | 9/2002 |
| WO | 03/086498 | A2 | 10/2003 |
| WO | 03086498 | A2 | 10/2003 |
| WO | 2004/023986 | A1 | 3/2004 |
| WO | 2006/116597 | A2 | 11/2006 |

OTHER PUBLICATIONS

EP Extended Search Report in corresponding Ep 10 159 373.9, dated Nov. 15, 2010.
EP Office Action in counterpart EP Application No. 10 159 373.9, dated Jul. 2, 2013.
Extended European Search Report for EP 14 185 045.3 dated Feb. 2, 2015.

* cited by examiner

LOCATABLE CATHETER

CROSS-REFERENCE TO RELATED APPLICATIONS

This application is a continuation application of U.S. patent Ser. No. 12/755,332 filed on Apr. 6, 2010 by Greenburg et al., now U.S. Pat. No. 8,611,984, which claims priority to U.S. Provisional Application Ser. No. 61/167,839 filed Apr. 8, 2009 entitled Locatable Catheter, which is hereby incorporated herein by reference in its entirety.

FIELD OF THE INVENTION

The field of the present invention pertains generally to the navigation of a device, such as a catheter, through a branched structure and the monitoring of a position of said device once a target location has been reached. More specifically, the present invention relates to a locatable catheter for navigating through body lumens and providing a delivery conduit for other devices.

BACKGROUND OF THE INVENTION

The most common interventional procedure in the field of Pulmonary Medicine (i.e., medicine pertaining to the respiratory system) is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source, an imaging assembly for delivering back a video image from the bronchoscope's distal tip, and a lumen or working channel through which instruments may be inserted, including but not limited to diagnostic (e.g., biopsy tools) and therapeutic (e.g., laser, cryo or RF tissue elimination probes) instruments. The distal tip of a bronchoscope is steerable and therefore rotating a lever placed at the handle of the bronchoscope actuates the steering mechanism by deflecting the tip in two opposite directions.

Bronchoscopes are limited, however, in how far they may be advanced through the airways due to their size. Typically, a bronchoscope is much wider than other types of catheters, mainly due to the size constraints placed on their design by the camera. Unfortunately, the lesion or target of interest is often located deeper in the lungs than a bronchoscope can travel. Hence, three-dimensional location technology has been developed that allow the navigation of a steerable catheter deep into the lungs. The catheter includes a sensor that can be detected magnetically with great precision. Of particular relevance to the present invention are the devices and methods described in the following references: PCT Patent Publication No. WO 03/086498 entitled "Endoscope Structure and Techniques for Navigation in a Branched Structure" to Gilboa; U.S. Pat. No. 7,233,820 entitled "Endoscope Structures And Techniques For Navigating To A Target In Branched Structure" to Gilboa; U.S. Pat. No. 6,947,788 entitled "Navigable Catheter" to Gilboa; U.S. Pat. No. 6,833,814 entitled "Intrabody Navigation System For Medical Applications" to Gilboa et al.; U.S. Pat. No. 6,711,429 entitled "System And Method For Determining The Location Of A Catheter During An Intra-Body Medical Procedure" to Gilboa et al.; U.S. Pat. No. 6,615,155 entitled "Object Tracking Using A Single Sensor Or A Pair Of Sensors" to Gilboa; U.S. Pat. No. 6,593,884 entitled "Intrabody Navigation System For Medical Applications" to Gilboa et al.; U.S. Pat. No. 6,380,732 entitled "Six-Degree Of Freedom Tracking System Having A Passive Transponder On The Object Being Tracked" to Gilboa; U.S. Pat. No. 6,188,355 entitled "Wireless Six-Degree-Of-Freedom Locator" to Gilboa; each of which is hereby incorporated by reference in its entirety.

These references describe methods and devices in which locatable guides ("LGs"), enveloped by sheaths, are used to navigate to a location within the lung. The guide/sheath combination is inserted into the lung via the working channel of a bronchoscope. Once the tip of the guide is located at its target, a lock, which is placed at the orifice ("connection port") of the bronchoscope's working channel, is operated to prevent the sheath from sliding in or out of the bronchoscope. The guide is then withdrawn from the sheath, leaving the sheath in place to guide a tool to the required target location.

Once the target has been reached with the LG, the LG is removed, leaving the sheath in place as a conduit to the target for other tools. However, the present design includes most or all of the location technology on the LG. Hence, once the LG is removed from the sheath, the physician is assuming that the sheath remains in close proximity to, and pointed at, the target.

OBJECTS AND SUMMARY OF THE INVENTION

The present invention addresses the identified needs by providing a locatable sheath that can be used in conjunction with, or instead of, an LG. Adding a sensor to a sheath adds the complication of maintaining an open lumen through the sheath. As such, various sensor designs are provided that do not interfere with the sheath lumen.

One aspect of the present invention provides a catheter sheath with a sensor at the distal tip. The sensor is comprised of three coils of wire, each at an angle to the others but sharing a common center point, in order to reduce the overall longitudinal dimension of the sensor. By reducing the longitudinal dimension, the impact the sensor has on the flexibility of the distal tip is minimized.

Another aspect of the present invention provides a catheter sheath with a sensor incorporated into a side of the sheath, such that the sensor is off-center. This design allows the entire sensor to be manufactured separate from the catheter and attached later as a component.

Yet another aspect of the present invention provides a sheath with a sensor that comprises a single coil at the distal tip and surrounding the lumen. This design greatly reduces the impact the sensor has on the flexibility of the sheath. The single coil design does not provide the degrees of freedom that a triple-coil design does but would be used in conjunction with an LG and, after the LG is removed, provides enough information to notify the physician that the sheath has moved out of position and needs to be adjusted.

DESCRIPTION OF EMBODIMENTS

Figure 1:
FIG. 1 is a perspective view of a preferred embodiment of the present invention; and, FIG. 2 is a perspective view of a preferred embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Turning now to the Figures and first to FIG. 1, there is shown a device 10 of the present invention. Device 10 generally comprises a locatable guide ("LG") 12 and a locatable sheath 20. It is understood that locatable sheath 20 could be used with or without LG 12. The LG 12 includes a sensor 14 embedded in a distal tip 16 thereof. The distal tip 16 is shown with a cutout in order to view the embedded sensor 14. Examples of LG 12 embodiments are shown and described in PCT Patent Publication No. WO 03/086498 entitled "Endoscope Structure and Techniques for Navigation in Branched Structure" to Gilboa, which is hereby incorporated by reference in its entirety.

These LG 12 embodiments are steerable probes that incorporate six degree-of-freedom ("6 DOF") sensors that operate by sensing externally-generated magnetic fields. For example, three magnetic fields may be generated, each using a separate frequency. The three magnetic fields vary in intensity throughout an operational area. Placing three orthogonally-oriented coils in the operational area results in signals generated by the coils that indicate three-dimensional location and three-dimensional orientation of the sensor 14.

The sheath 20 includes one or more coils 22 that are either embedded in its wall or are attached to an outside surface thereof. The sheath 20 also defines a central lumen 24 that is unobstructed by the coils 22. One embodiment of the sheath 20 includes only a single coil 22 proximate its distal tip 26. The coil 22 is used to generate signals indicating its location in a variety of ways.

For example, the single coil can generate signals using the same magnetic fields utilized by the LG 12. Hence, after the LG 12 is removed, the single coil 22 may be used to generate a signal indicating its three-dimensional location in the operational field.

Alternatively, a field may be generated on a fourth frequency such that the sensor 22 may be used concurrently with the sensor 14 of the LG 12. If the sensor 22 is dedicated to a single field on a fourth frequency, the sensor would not be useful for three-dimensional position data but could be used to generate a signal indicating that it has moved out of position after the LG 12 is withdrawn.

Another embodiment, shown in FIG. 1, utilizes multiple coils 22. The coils 22 are spaced apart along the length of the sheath 20. The coils 22 provide position data of various points along the length of the sheath 20, thereby "painting a picture" of the sheath. As such, even though the coils 22 are not providing 6 DOF data, when viewed together they provide an indication of the location and orientation of the sheath 20. Hence, this embodiment of sheath 20 may be used to both navigate to the target and provide a conduit for tools, possibly obviating the need for the LG 12.

Figure 2:
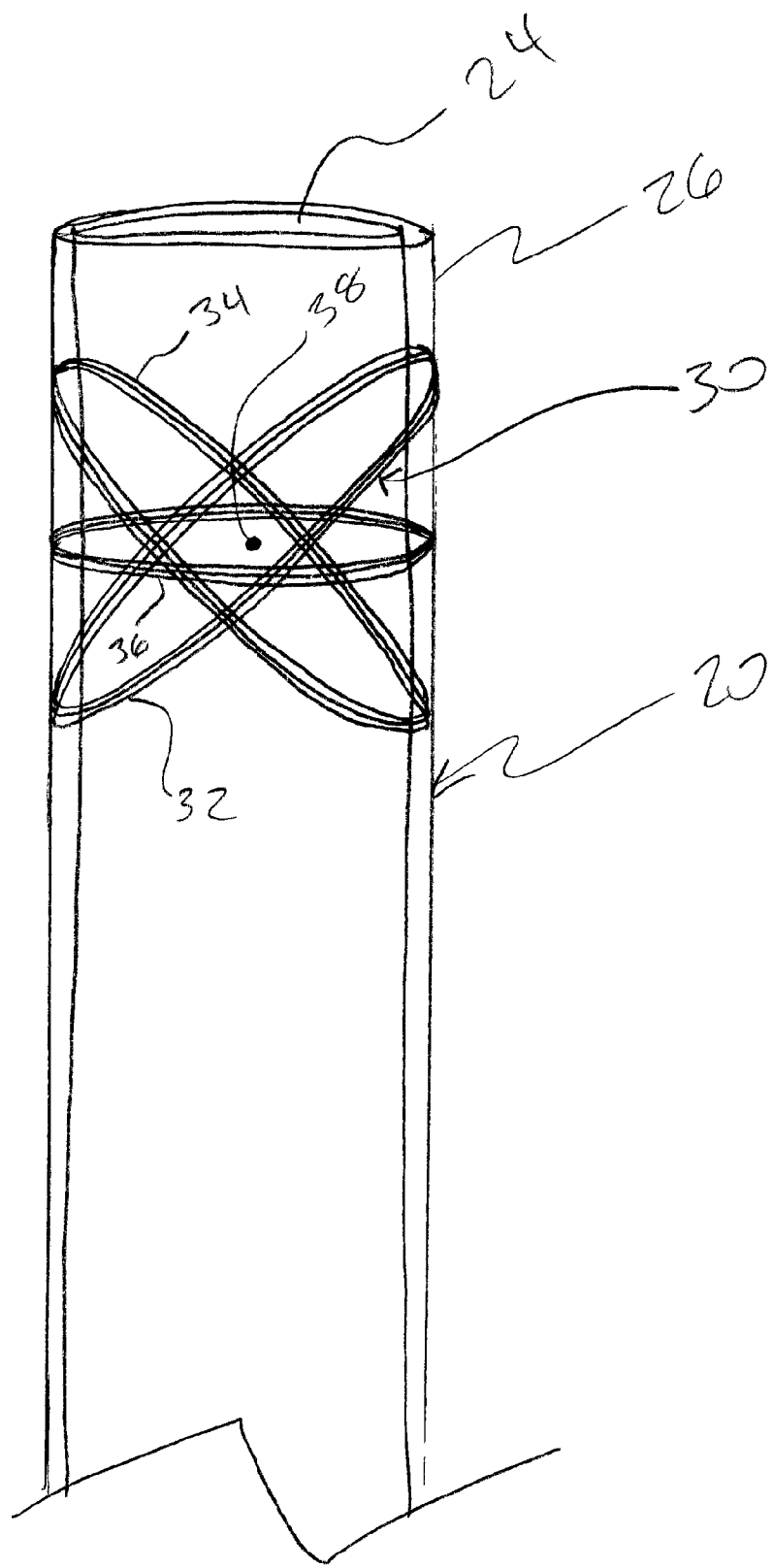

Referring now to FIG. 2, there is shown an embodiment of a sheath 20 with a 6 DOF sensor 30 incorporated into its distal tip 26. The sheath 20 is shown as transparent such that the details of the sensor 30 may be more easily displayed. The sensor 30 includes three coils 32, 34 and 36. Coils 32 and 34 are angled, while coil 36 is relatively circumferential to the sheath 20. Preferably, coils 32 and 34 lie in planes that are relatively perpendicular to each other. More preferably, all three coils share a common center point 38. By sharing a common center point 38, the longitudinal dimension of the overall sensor is minimized, thereby reducing the impact of the sensor 30 on the flexibility of the sheath 20. This design represents an advantage over prior art designs, such as that shown and described in International Publication Number WO 97/29684, to Acker. Acker discloses several coil designs that leave a central lumen open but are longitudinally extended, resulting in a reduced flexibility of the catheter in order to maintain a constant spatial relationship between the coils.

Although the invention has been described in terms of particular embodiments and applications, it should be appreciated that other embodiments and applications also fall within the scope of the present invention. One of ordinary skill in the art, in light of the teaching, can generate embodiments and modifications without departing from the spirit of or exceeding the scope of the claimed invention.

For example, each of the embodiments is described as having sensors incorporated into a sheath 20 that are passive. In other words, the described sensors generate signals when they pass through magnetic fields or reside within an electromagnetic field. However, one skilled in the art will understand that any or all of the coils of the sensors could be actively energized to generate magnetic fields. The generated magnetic fields could then be detected by external passive sensors and used to calculate a position and/or orientation of the coil(s). Accordingly, it is to be understood that the drawings and descriptions herein are proffered by way of example to facilitate comprehension of the invention and should not be construed to limit the scope thereof.

What is claimed is:

1. A locatable medical instrument insertable through a working channel of a bronchoscope, comprising:
   a sheath having at least three coils embedded therein, the at least three coils overlying one another and having a common center point, and each of the at least three coils is integrally formed within a wall defining a longitudinal lumen extending through the sheath,
   wherein each of the at least three coils is configured to generate a signal when placed in an electromagnetic field, the signal indicative of a strength of the electromagnetic field and the position of the sheath; and
   wherein two of the at least three coils are approximately perpendicular to each other.

2. The locatable medical instrument of claim 1, wherein the sheath includes a generally elongated configuration and is flexible.

3. The locatable medical instrument of claim 1, wherein the sheath includes a distal end configured to receive a probe therethrough for positioning the sheath adjacent target tissue.

4. The locatable medical instrument of claim 3, wherein the at least three coils are positioned proximate the distal end of the sheath.

5. A system for navigating through a branched structure, comprising:
   a sheath having embedded therein a first electromagnetic field sensor configuration including at least three coils overlying one another and sharing a common center point, and each of the at least three coils is integrally formed within a wall defining a longitudinal lumen extending through the sheath;
   a probe extendable through the lumen of the sheath and having a second electromagnetic field sensor embedded within a distal tip thereof;
   an electromagnetic field generation device configured to create electromagnetic fields having a plurality of frequencies and configured to induce signals in the first and second electromagnetic field sensors, wherein the first electromagnetic field sensor is configured to generate signals indicating its position relative to the branched structure; and wherein two of the at least three coils are approximately perpendicular to each other.

6. The system of claim 5, wherein the first electromagnetic sensor is positioned proximate a distal end of the sheath.

7. The system of claim 5, wherein the first electromagnetic field sensor comprises a six degree-of-freedom sensor.

8. The system of claim 5, wherein the second electromagnetic field sensor comprises a six degree-of-freedom sensor.

9. The system of claim 5, wherein the electromagnetic field generation device creates electromagnetic fields of at least four frequencies, three of the at least four frequencies detected by the second electromagnetic field sensor, thereby allowing the second electromagnetic field sensor to generate six degree-of-freedom location information.

10. The system of claim 9 wherein one of the at least four frequencies is detected by the first electromagnetic field sensor, thereby allowing the first electromagnetic field sensor to generate a signal including location information.

11. A method for accessing a target in a branched structure, comprising:

providing an electromagnetic field generator defining a sensing volume containing the branched structure;

advancing a probe through the branched structure, the probe including a probe electromagnetic field sensor configured to sense electromagnetic fields generated by the electromagnetic field generator and creating probe location signals as a result to locate the target;

advancing a sheath over the probe to the target, the sheath at its distal end having at least three coils embedded therein and overlying one another so as to share a common center point, and each of the at least three coils is integrally formed within a wall defining a longitudinal lumen extending through the sheath, the at least three coils configured to sense electromagnetic fields generated by the electromagnetic field generator and creating sheath location signals as a result;

removing the probe proximally from the sheath;

monitoring a location of the sheath using the sheath location signals to ensure the distal end of the sheath remains at the target; and accessing the target with one or more instruments by passing the one or more instruments through the sheath;

wherein two of the at least three coils are approximately perpendicular to each other.

12. The method of claim 11 wherein monitoring the location of the sheath further includes reading signals from the at least three coils on the sheath at a frequency that is independent of frequencies of signals from the electromagnetic field sensor on the probe.

13. The method of claim 11 wherein monitoring the location of the sheath further includes reading signals from the at least three coils on the sheath at a frequency that is the same as frequencies of signals from the electromagnetic field sensor on the probe.

* * * * *